(12) United States Patent
Giraud et al.

(10) Patent No.: US 10,639,421 B2
(45) Date of Patent: May 5, 2020

(54) METHODS AND APPARATUSES FOR INJECTION MOLDING WALLED STRUCTURES

(71) Applicant: SiO2 Medical Products, Inc., Auburn, AL (US)

(72) Inventors: Jean-Pierre Giraud, Aubrun, AL (US); Herve Pichot, Chennevieres-sur-Marne (FR)

(73) Assignee: SiO2 Medical Products, Inc., Auburn, AL (US)

( * ) Notice: Subject to any disclaimer, the term of this patent is extended or adjusted under 35 U.S.C. 154(b) by 700 days.

(21) Appl. No.: 15/027,165

(22) PCT Filed: Oct. 15, 2014

(86) PCT No.: PCT/US2014/060586
§ 371 (c)(1),
(2) Date: Apr. 4, 2016

(87) PCT Pub. No.: WO2015/057769
PCT Pub. Date: Apr. 23, 2015

(65) Prior Publication Data
US 2016/0235914 A1 Aug. 18, 2016

Related U.S. Application Data

(60) Provisional application No. 61/891,064, filed on Oct. 15, 2013, provisional application No. 62/048,725, filed on Sep. 10, 2014.

(51) Int. Cl.
*A61M 5/19* (2006.01)
*B05D 1/00* (2006.01)
(Continued)

(52) U.S. Cl.
CPC ............ *A61M 5/19* (2013.01); *A61M 5/2448* (2013.01); *A61M 5/284* (2013.01);
(Continued)

(58) Field of Classification Search
CPC .... A61M 5/19; A61M 5/31596; A61M 5/284; A61M 5/2448; A61M 2207/00;
(Continued)

(56) References Cited

U.S. PATENT DOCUMENTS 2,591,046 A 4/1952 Brown
4,130,264 A 12/1978 Schroer
(Continued)

FOREIGN PATENT DOCUMENTS

DE 10356335 A1 6/2005
EP 1972355 A1 9/2008
(Continued)

OTHER PUBLICATIONS

International Search Report and Written Opinion dated Jan. 30, 2015 relating to PCT/US2014/060586.
(Continued)

*Primary Examiner* — Robert J Grun
(74) *Attorney, Agent, or Firm* — David B. Gornish; Eckert Seamans Cherin & Mellott, LLC

(57) ABSTRACT

A process is provided for making a walled structure using an injection molding apparatus. The apparatus has a molding space formed between a mold cavity and an inner core disposed within the mold cavity. The molding space defines a shape of the structure. The process includes injecting molding material into the molding space, moving or retaining a portion of a movable impression member protruding from the inner core within a portion of the molding space so as to create a recess within an inner wall of the structure, and retracting the impression member into the inner core such
(Continued)

that the impression member is cleared from the molding space.

20 Claims, 11 Drawing Sheets

(51) Int. Cl.
| | |
|---|---|
| *B29C 45/26* | (2006.01) |
| *A61M 5/315* | (2006.01) |
| *A61M 5/28* | (2006.01) |
| *B29C 45/44* | (2006.01) |
| *A61M 5/24* | (2006.01) |
| *B29L 31/00* | (2006.01) |
| *B29K 101/12* | (2006.01) |

(52) U.S. Cl.
CPC ........... *A61M 5/31596* (2013.01); *B05D 1/62* (2013.01); *B29C 45/2614* (2013.01); *B29C 45/44* (2013.01); *A61M 2207/00* (2013.01); *B29K 2101/12* (2013.01); *B29K 2995/0026* (2013.01); *B29L 2031/7544* (2013.01)

(58) Field of Classification Search
CPC ....... B05D 1/62; B29C 45/2614; B29C 45/44; B29K 2995/0026; B29K 2101/12; B29L 2031/7544
See application file for complete search history.

(56) References Cited

U.S. PATENT DOCUMENTS

| | | |
|---|---|---|
| 5,605,542 A | 2/1997 | Tanaka et al. |
| 5,788,670 A | 8/1998 | Reinhard et al. |
| 6,817,987 B2 | 11/2004 | Vetter et al. |
| 7,985,188 B2 | 7/2011 | Felts et al. |
| 2004/0079885 A1 | 4/2004 | Hamamoto et al. |
| 2008/0230961 A1 | 9/2008 | Moesli et al. |
| 2009/0232932 A1* | 9/2009 | Togashi .............. B29C 45/7312 425/577 |
| 2013/0200549 A1* | 8/2013 | Felts .................. A61M 5/3129 264/275 |
| 2013/0291632 A1 | 11/2013 | Felts et al. |
| 2014/0171862 A1 | 6/2014 | Weidner |

FOREIGN PATENT DOCUMENTS

| | | |
|---|---|---|
| EP | 2060376 A1 | 5/2009 |
| GB | 705392 | 3/1954 |
| JP | 8132444 A | 5/1996 |
| JP | 2007260349 A | 10/2007 |

OTHER PUBLICATIONS

International Search Report and Written Opinion dated Jun. 22, 2016 relating to PCT/US2016/026122.

* cited by examiner

METHODS AND APPARATUSES FOR INJECTION MOLDING WALLED STRUCTURES

CROSS-REFERENCE TO RELATED APPLICATIONS

This application is a U.S. National Phase of International Application No. PCT/US2014/060586 filed Oct. 15, 2014, which claims priority to U.S. Provisional Patent Application Nos. 61/891,064 filed Oct. 15, 2013; and 62/048,725 filed Sep. 10, 2014 which are incorporated herein by reference in their entireties.

FIELD OF INVENTION

The present invention relates to methods and apparatuses for injection molding walled structures having one or more openings, such as syringes, cartridges, containers, vials and the like. More particularly, the present invention is directed to creating, via injection molding, one or more recesses in an internal wall of a structure without altering the surface geometry of the external wall of that structure. Methods and apparatuses according to the invention may be used to create, e.g., a dual-chambered medical barrel (e.g., syringe barrel) having a bypass groove within the inner wall that does not cause the adjacent outer wall to bulge outwardly.

BACKGROUND OF THE INVENTION

As a prelude to describing products and processes according to the present invention, some background on the fields of dual-chambered syringes and injection molding techniques for medical barrels and other such thin-walled tubular structures, is appropriate.

Dual-chambered syringes, such as those described in U.S. Pat. Nos. 5,605,542 and 6,817,987, which are incorporated herein by reference in their entireties, typically include a tubular barrel with an axially movable partition disposed within the barrel. The partition separates and seals off front and rear syringe chambers, one from the other. The purpose of these separate chambers is to enable the syringe to hold two separate substances, which are generally combined by actuating the syringe at the time of use. For example, the front chamber may contain a lyophilized drug product and the rear chamber may contain a liquid solvent to be mixed with the drug product at the time of use. By maintaining these substances in separate chambers until the time of use, the stability of the preparation may be improved.

When the syringe is actuated at the time of use, the partition moves axially, towards the front of the syringe (i.e., towards the needle). In order to enable fluid communication between front and rear chambers at the time of use, a dual-chambered syringe typically has a bypass groove along a portion of the syringe's inner wall. The bypass groove tends to have a length that exceeds the length of the partition. As such, when the partition is driven forward and seated over the bypass groove, fluid from one chamber is permitted to flow around the partition via the bypass groove into the other chamber, thereby combining the two substances that were initially segregated.

As shown in FIG. 1, which is a reproduction of FIG. 1 from U.S. Pat. No. 5,605,542, the bypass groove of the syringe (reference numeral 6 in that figure) is a recess in the syringe barrel that is formed by a bulging of the outer wall of the barrel. Likewise, as shown in FIG. 2, which is a reproduction of FIG. 1 from U.S. Pat. No. 6,817,987, the outer wall of the syringe barrel adjacent to the bypass groove (reference numeral 9 in that figure) bulges outwardly. This appears to be typical configuration for bypass grooves in the dual-chambered syringe art. While this configuration may be suitable for syringes made from glass, there are challenges associated with producing plastic dual-chambered syringes having functional bypasses with good flow properties. These challenges arise from the nature of typical injection molding processes used for making plastic syringe bodies. To better convey the nature of such challenges, a background on the injection molding process, as it pertains to medical barrels (e.g., syringes), is now provided.

FIG. 3 illustrates an exemplary embodiment of a molding assembly for molding a thin-walled plastic tubular structure, e.g., a syringe barrel. An exemplary syringe barrel 12 that may be molded using the molding assembly is shown in FIGS. 4 and 5.

The molding assembly includes one or more mold cavities 142. The mold cavity 142, shown in detail in FIG. 3, is configured for molding a syringe barrel 12 of the type shown in FIGS. 4 and 5, although it should be understood that the mold cavity 142 may be modified to produce similar tubular thin-walled structures other than syringe barrels, e.g., cartridges, parenteral containers, and the like.

The mold cavity 142 is formed as a cylindrical opening 144 in a molding block of the assembly. The opening 144 extends in direction D to an inner surface 146 of the molding block. A sleeve 148 may be fitted within the molding block and define the opening 144. The sleeve 148 is formed of a material capable of appropriately distributing heat during molding and may include a plurality of cooling channels 150.

An inner core 152 fits within the opening 144 to define the interior 20 of the syringe barrel 12. The inner core 152 is of a cylindrical shape similar to that of the opening 144, but is of a smaller diameter. A molding space 154 is defined between the opening 144 and the inner core 152. The molding space 154 is sized and shaped to form a syringe barrel 12, such as that shown in FIGS. 4 and 5. The inner core 152 projects from a core plate, which is located outward in the molding assembly with respect to the molding block. An injector 156 extends through a portion of the molding block for injecting thermoplastic molding material (e.g., a cyclic olefin) into the mold cavity 142 during molding.

Upon initiation of a molding operation, a core plate is first moved in direction D, such that the inner core 152 is moved into the opening 144, to create a syringe barrel 12 shaped molding space 154. Molten molding material is then injected into the mold cavity 142 through the injector 156. The molding assembly may be heated before or during this portion of the procedure to permit sufficient flow of the molding material to fill the entire molding space 154. The molding material flows through the molding space 154.

The molding material is then permitted to cool below its melting point, and in some embodiments may be actively cooled by cooling of the assembly, for example by injecting a coolant into cooling channels 150 where provided. The core plate is moved outward in direction D, withdrawing the core 152 from the interior 20 of the molded syringe barrel 12. The syringe barrel 12 is withdrawn from the mold cavity 142 by being moved outward in direction D, i.e., in a direction along the axis of the syringe barrel 12.

Injection molding is the most common and preferred method of fabricating plastic parts because of its speed of production, low labor costs and design flexibility. As mentioned above, however, there are challenges to incorporating a standard, outwardly protruding bypass, in a plastic injection molded syringe barrel. One such challenge is that an outward protrusion or bulge from the outer wall of the syringe barrel would prevent the syringe from being withdrawn from the mold cavity in a direction along the axis of the syringe barrel. While a mold cavity may be configured to create a protrusion from the outer wall of the syringe, such a mold would need to be formed from two mold blocks joined together. Once a syringe barrel is formed and cooled, the mold blocks would separate enabling withdrawal of the syringe barrel. This process, however, would imprint a line on the syringe barrel along the seam in which the mold blocks had been joined. Syringe bodies often need to be transparent and unblemished to enable visual inspection of the nature of the syringe's contents (e.g., to confirm that no particulates are suspended therein, etc.). A line along the syringe barrel or other visual blemishes could frustrate this purpose. While withdrawal of the syringe barrel from a solid one-piece mold cavity in an axial direction avoids the problem of the line blemish, an outward protrusion on an injection molded syringe barrel prevents withdrawal of the syringe barrel in an axial direction for reasons discussed above.

What is needed, therefore, is a plastic injection molded syringe barrel with a bypass in the inner wall that does not cause the outer wall to bulge outwardly. More broadly, what is needed are methods and apparatuses for injection molding a walled structure, in which one or more recesses (including a bypass groove having good flow properties) are impressed into an inner wall of the structure without altering the surface geometry of the outer wall of the structure.

The foregoing Background of the Invention should be regarded as part of the specification of the invention. It is intended that components, elements and aspects of dual chambered syringes, injection molding apparatuses and processes for injection molding described in the Background of the Invention may be used as support for aspects of the claimed invention.

BRIEF SUMMARY OF THE INVENTION

Accordingly, in one aspect, the present invention is directed to a dual-chambered cartridge or syringe comprising a thermoplastic barrel having an inner wall and an outer wall, the inner wall comprising a bypass groove, wherein the outer wall adjacent to the bypass groove is unaltered by the bypass groove.

In another aspect, the present invention is directed to a process for making a thermoplastic walled structure using an injection molding apparatus. The apparatus has a molding space formed between a mold cavity and an inner core disposed within the mold cavity. The molding space defines a shape of the structure. The process includes injecting molding thermoplastic material into the molding space, moving or retaining a portion of a movable impression member protruding from the inner core within a portion of the molding space so as to create a recess within an inner wall of the structure, and retracting the impression member into the inner core such that the impression member is cleared from the molding space and optionally housed entirely within the inner core.

In yet another aspect, the present invention is directed to an apparatus for injection molding walled structures. The apparatus includes a mold block having within it a mold cavity. An inner core is disposed within the mold cavity and a molding space exists between the inner core and the mold cavity. The molding space defines a predetermined shape of a structure that may be fabricated from thermoplastic molding material injected into the molding space. The inner core includes an impression member that is movable from an extended position, wherein a portion of the impression member protrudes into the molding space, to a retracted position wherein the impression member is cleared from the molding space and optionally housed entirely within the inner core.

In another aspect, the present invention is directed to an apparatus for injection molding medical barrels, the apparatus including a mold block having within a mold cavity within the mold block. An inner core is disposed within the mold cavity and there is a molding space between the inner core and the mold cavity. The molding space defines a predetermined shape of a structure that may be fabricated from molten thermoplastic molding material injected into the molding space. The inner core has an impression member that is movable in a direction perpendicular to the central axis of the inner core, from an extended position wherein a portion of the impression member protrudes into the molding space, to a retracted position wherein the impression member is cleared from the molding space and is housed entirely within the inner core. Optionally, movement of the impression member perpendicular to the central axis of the inner core is driven by axial movement of the actuator.

DETAILED DESCRIPTION OF THE INVENTION

Bypass Syringe and Process for Molding the Same

In one aspect, the invention is directed to processes and apparatuses for fabricating medical barrels (sometimes simply referred to herein as "barrels") through injection molding. As used herein, "medical barrel" refers to a generally tubular vessel adapted for medical use, the vessel having at least one opening at an end thereof (and preferably another opening at an opposite end). Examples of medical barrels include barrels for syringes, pre-filled syringes, cartridges, prefilled cartridges, auto-injectors and other such parenteral packages. While a preferred application of the invention, as discussed below, relates to medical syringes, it should be understood that the invention is not limited to syringes, but may include any medical barrel. The invention also broadly extends to processes and apparatuses used for injection molding undercuts or impressions on the inner walls of other types of containers (e.g. vials).

Figure 6:
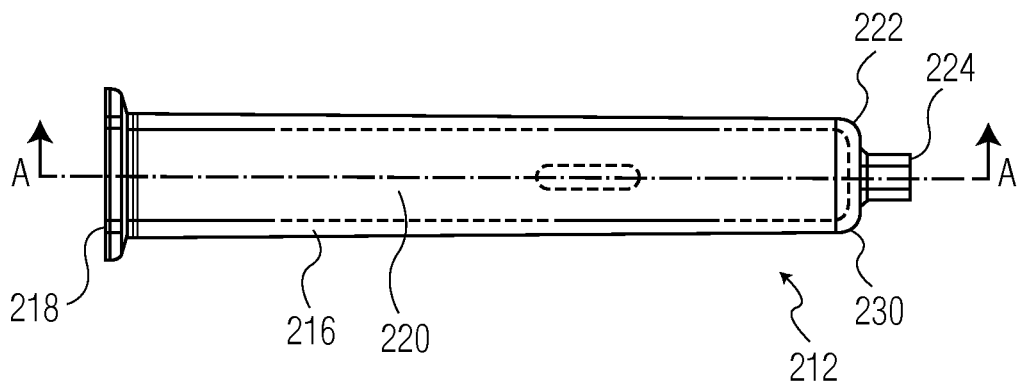
FIG. 6 is a side elevational view of a syringe barrel according to the present invention.
Figure 7:
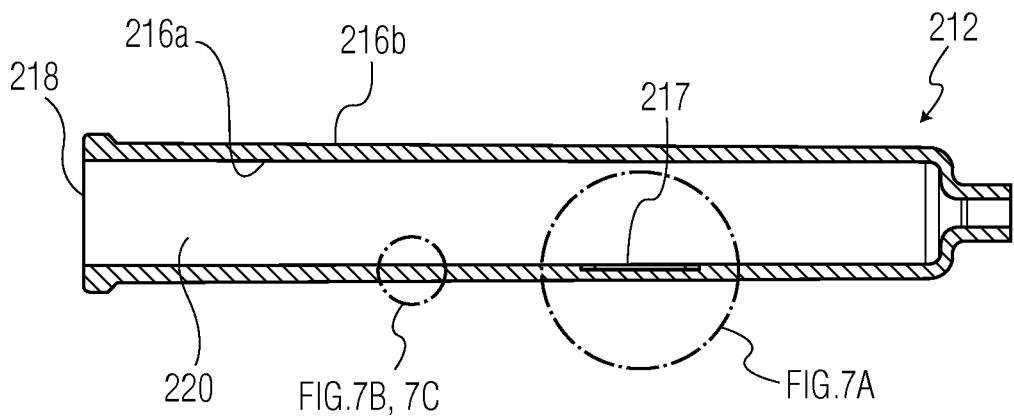
FIG. 7 is a cross sectional view along line A-A of FIG. 6.
Figure 7A:
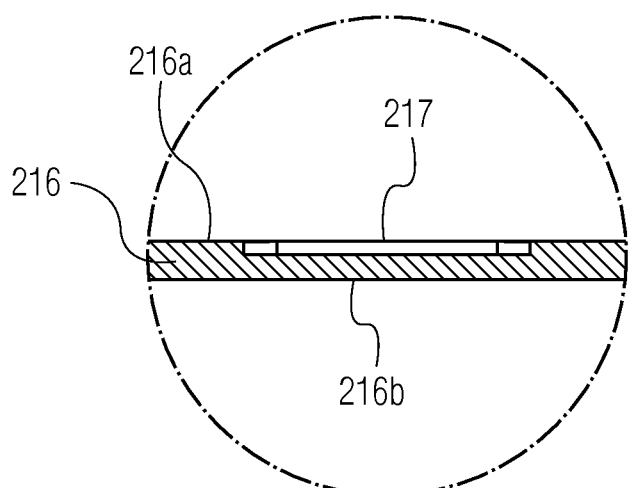
FIG. 7A is an enlarged view of a bypass groove in the wall of the syringe barrel shown in FIG. 7.

Referring now to FIGS. 6-7A, there is shown an exemplary syringe barrel 212 according to an aspect of the present invention. The syringe barrel 212 is formed as a generally tubular wall 216 with an opened first end 218 leading to an interior 220. Along a portion of the inner wall 216a of the syringe barrel 212 is a recessed longitudinal bypass groove 217. Notably, unlike typical dual-chambered syringe configurations, particularly those made from glass, the outer wall 216b adjacent to the bypass groove 217 does not bulge outwardly, thus leaving that section of the outer wall 216b unaltered. In other words, the bypass groove 217 does not alter the surface geometry of the outer wall 216b adjacent to the bypass groove 217. In use, plungers and a sealing partition may be slidably housed within the interior 220 of the syringe barrel 212 to create a dual-chambered syringe, wherein the initial position of the partition would be between the first end 218 and the bypass groove 217. Such a configuration would enable a syringe made from the syringe barrel 212 to contain two separate substances that could be combined at the time of use, as described above regarding dual-chambered syringes. A needle receiving hub 224 protrudes from the second end 222 of the barrel 212, outward from an outward convexly curved end wall 230. In use, a needle may extend through the hub 224 from the exterior to the interior 220 of the hub 224, for transmitting an injectable material out from the syringe and into a patient.

The syringe barrel 212 is preferably fabricated from one or more thermoplastic materials that appear clear and glass-like in final form. Such materials include, for example cyclic olefin polymers (COP), cyclic olefin copolymers (COC) and polycarbonate. While it is preferable that the barrel material be clear in appearance for certain applications, the invention is not limited to clear plastics, but may include other polymers, for example, PET, polystyrene and polypropylene.

An advantage of the bypass grove 217 being housed entirely within the inner wall 216a of the syringe barrel 212 (i.e., without bulging outward from the outer wall 216b) is that the final syringe retains the tubular appearance and outer profile of a standard (i.e., non-dual-chambered) syringe. An additional advantage relates to the manner in which the syringe barrel 212 may be fabricated, discussed now.

Figure 1:
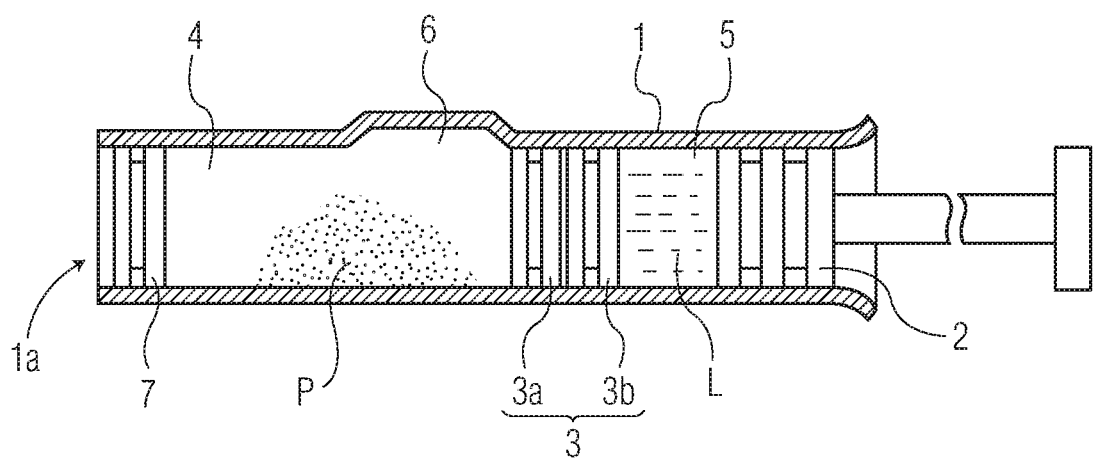
FIG. 1 is a schematic cross sectional view of an embodiment of a syringe illustrated in FIG. 1 of U.S. Pat. No. 5,605,542.
Figure 2:
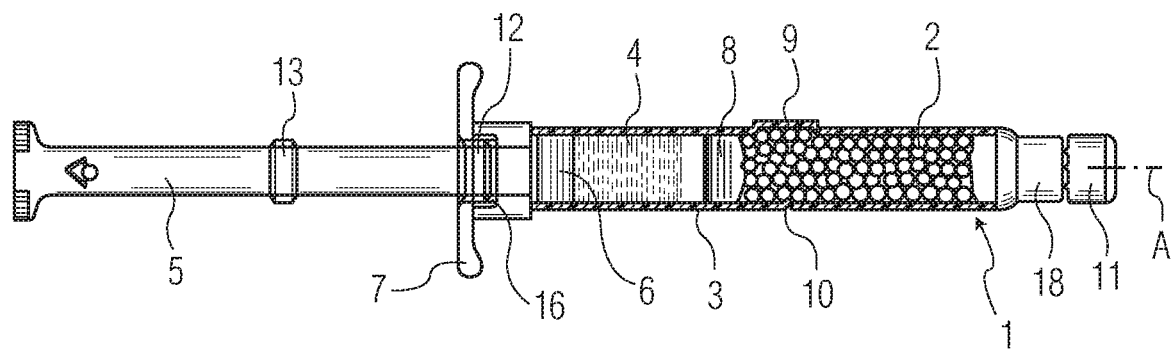
FIG. 2 is an axial section of a dual-chamber syringe illustrated in FIG. 1 of U.S. Pat. No. 6,817,987.
Figure 3:
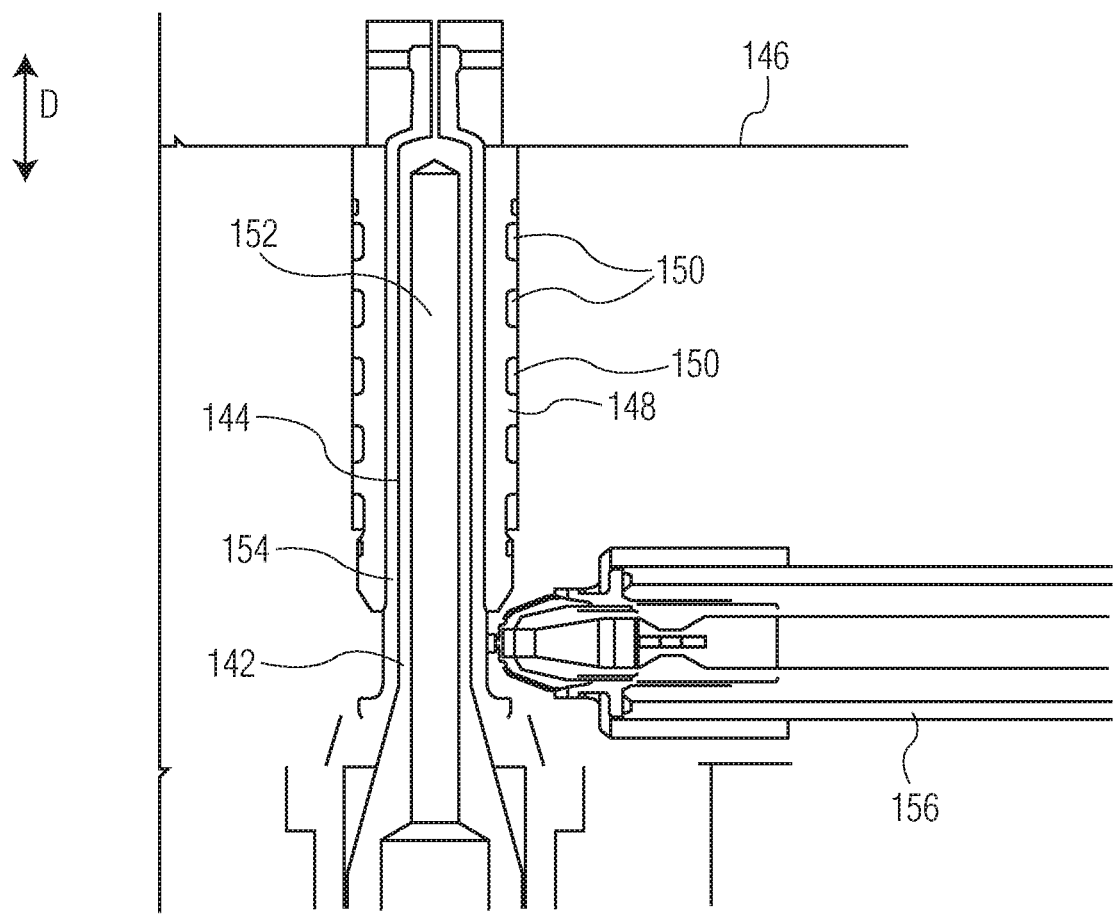
FIG. 3 is a cross sectional view of a portion of a molding assembly.
Figure 4:
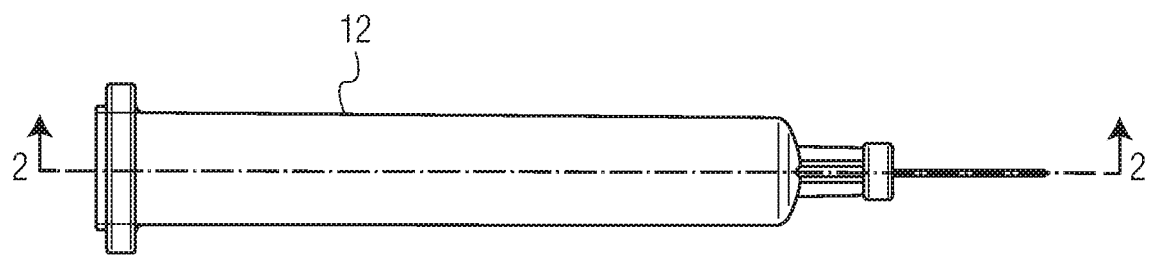
FIG. 4 is a side elevational view of a syringe barrel.
Figure 5:
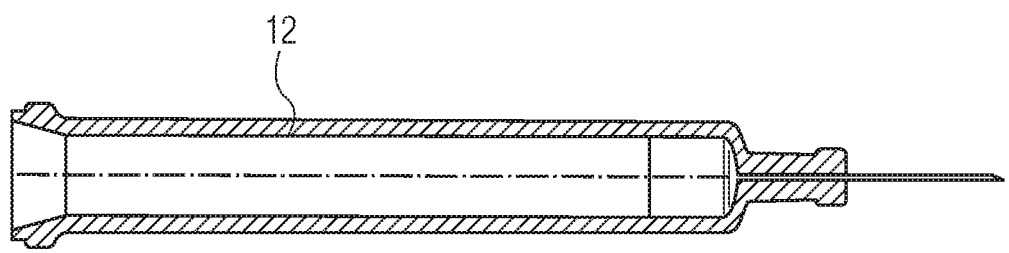
FIG. 5 is a cross sectional view along line 2-2 of FIG. 4.

To fabricate the syringe barrel 212 by injection molding, the equipment and process steps are similar in many respects to those used to create the syringe barrel 12 shown in FIGS. 4 and 5, which may be molded using the molding assembly shown in FIG. 3. However, to create an internal recess such as the bypass grove 217, which does not bulge outwardly from the outer wall 216b of the syringe barrel 212, a retractable structure (e.g. an impression member) may be provided from within the inner core of the molding assembly to create an impression or recess within the inner wall 216a.

Figure 8:
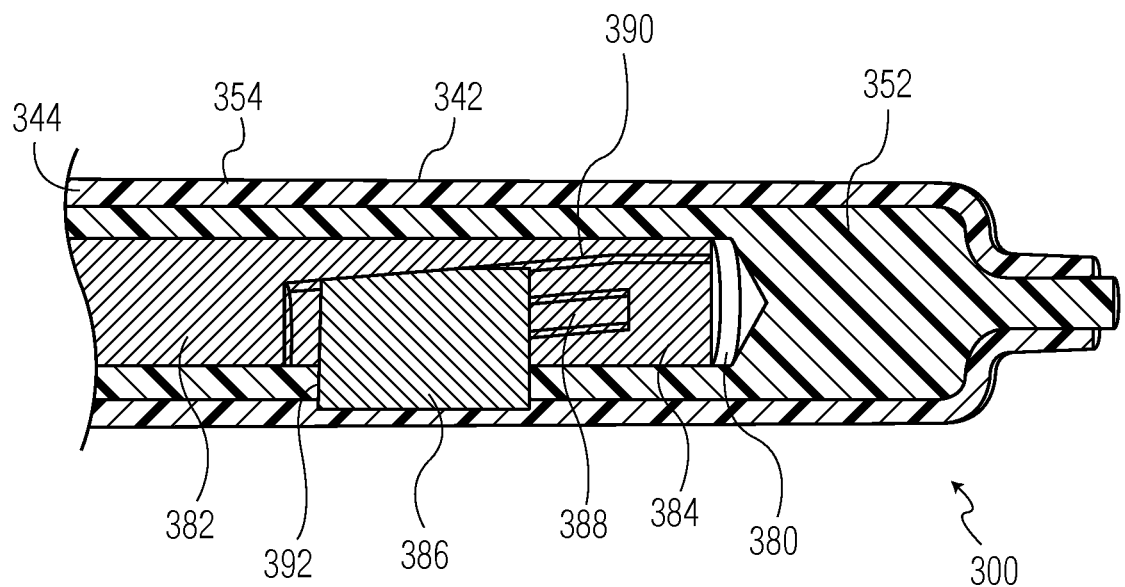
FIG. 8 is an enlarged partial cross sectional view of an injection molding apparatus for molding a syringe barrel with an actuator in an extended position.
Figure 9:
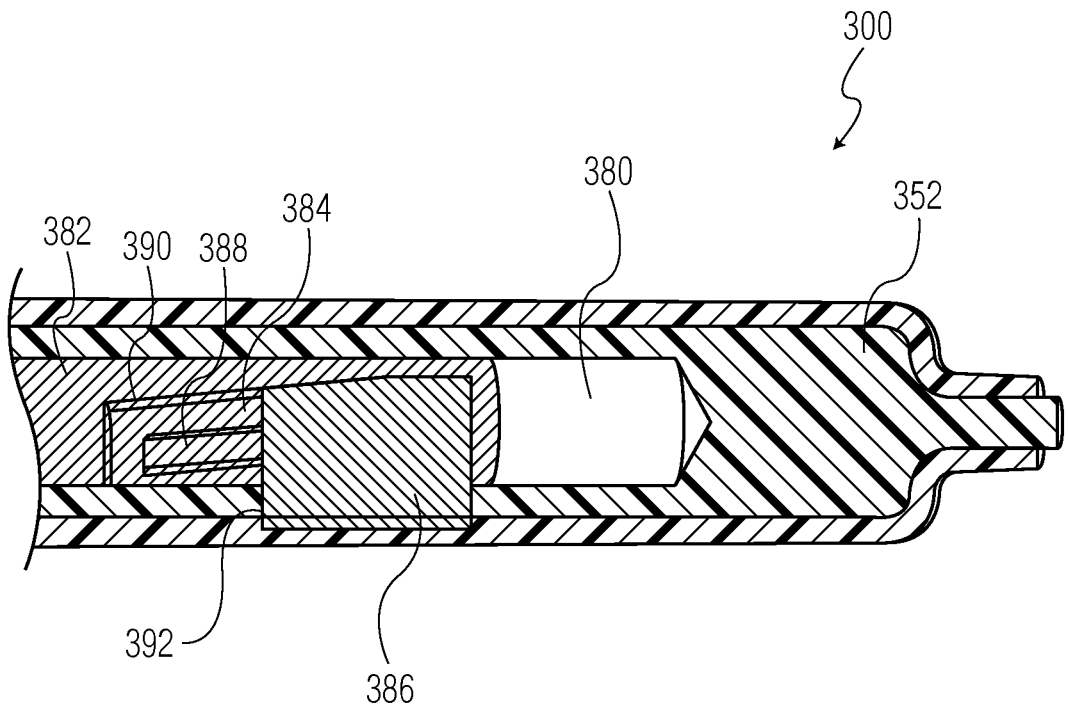
FIG. 9 is an enlarged partial cross sectional view of the injection molding apparatus of FIG. 8 with the actuator in a retracted position.

For example, referring to FIGS. 8 and 9, there is shown an injection molding apparatus 300 for molding a thin-walled tubular structure (e.g., a syringe barrel 212) having an impression or recess within the inner wall of the structure, such as a bypass groove 217. The apparatus 300, which may be integrated into, e.g., the molding assembly described above and shown in FIG. 3, includes a mold cavity 342 adapted to receive molten thermoplastic material for forming a syringe barrel 212. The mold cavity 342 is optionally constructed of a solid one-piece mold block as opposed to being formed from joining together two separate mold blocks. This feature would enable the syringe barrel 212 to be axially withdrawn once it is complete, without separating the mold blocks. In this way, one may avoid imprinting a line on the syringe barrel along the seam in which the mold blocks had been joined, as discussed above.

Figure 10:
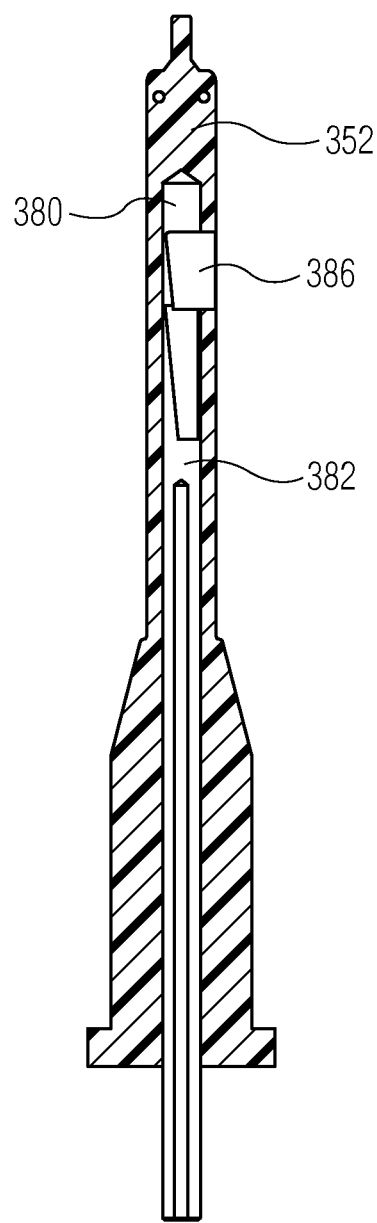
FIG. 10 is a cross sectional view of the inner core of the injection molding apparatus of FIG. 9.

The mold cavity 342 is formed from a cylindrical opening 344 of a molding block of the molding assembly. An inner core 352, of which a cross sectional view is shown in FIG. 10, fits within the opening to define the interior 220 of the syringe barrel 212. The inner core 352 is of a cylindrical shape similar to that of the opening 344, but is of a smaller diameter. A molding space 354 is defined between the opening 344 and the inner core 352. The molding space 354 is sized and shaped to form a syringe barrel 212, such as that shown in FIGS. 6-7A. To fabricate the syringe barrel 212, melted thermoplastic material is injected into the molding space 354.

Within the inner core 352 is a longitudinal space 380. An actuator 382 is disposed within the space 380 and is axially movable within the space 380. The actuator 382, which can be driven, e.g., pneumatically, electrically or hydraulically, may be slidable from an extended position within the space 380, as shown in FIG. 8, to a retracted position, as shown in FIG. 9. The actuator 382 may include a slot portion 384 having an impression member 386 disposed therein. A portion of the impression member 386 is slidably disposed within a track 388 which runs axially along a portion of the actuator 382 at a slight incline. The slot portion 384 further includes a ramp 390, the majority of which comprises an incline substantially parallel to the track 388.

In use, when the actuator 382 is in an extended position, as shown in FIG. 8, the impression member 386 is seated on a raised section of the ramp 390. In this position, the impression member 386 protrudes slightly through a window 392 in the inner core 352 and presses into the molten plastic in the molding space 354 to form a recess in the inner wall 216a of the syringe barrel 212. This recess constitutes the internal bypass groove 217, e.g., as shown in FIGS. 6-7A, in the completed syringe barrel 212. In a preferred embodiment, the impression member 386 moves perpendicular to the axial direction of movement of the actuator 382. In other words, movement of the impression member 386 perpendicular to the axial direction of movement of the actuator 382 and/or perpendicular to the central axis of the inner core 352, is driven by axial movement of the actuator 382. In this way, the bypass groove 217 is perpendicular, as opposed, e.g., to oblique, to the center axis of the syringe barrel 212. This enables the creation of a bypass groove 217 having a substantially constant cross section—a feature which the inventors submit would not be attainable were the impression member 386 to move in a direction that is not perpendicular (e.g., oblique) to the axial direction of movement of the actuator 382. This feature may allow for better control of the shape of the bypass groove 217 for improved fluid flow through the bypass groove 217, when used to mix components of a dual chambered syringe.

As discussed above, this bypass groove 217 is located entirely within the inner wall 216a and does not bulge outwardly from the outer wall 216b. When the actuator 382 is in its retracted position, as shown in FIG. 9, the impression member 386 is seated on a lowered section of the ramp 390. In this position, the impression member 386 is withdrawn from the molten plastic and its profile is contained entirely within the inner core 352. Thus, in one aspect, the present invention is directed to an impression member 386 which is movable from an extended position wherein a portion of the impression member 386 protrudes into the molding space 354, to a retracted position wherein the impression member 386 is cleared from the molding space 354 and optionally housed entirely within the inner core 352. Again, the impression member 386 may move from the extended position to the retracted position in a direction perpendicular to the axial direction of movement of the actuator 382 and/or perpendicular to the central axis of the inner core 352. Since the impression member 386, as shown in FIG. 9, does not interfere with the material in the molding space 354, when the syringe barrel 212 is sufficiently cool and thus in solid form, the syringe barrel 212 may be withdrawn from the molding apparatus 300 in an axial direction.

Figure 11A:
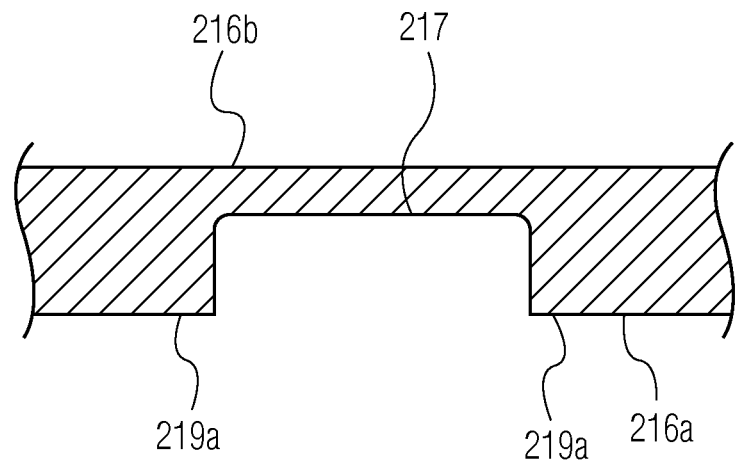
FIG. 11A is an enlarged cross sectional view of a bypass groove having sharp outer edges.

Thus, the molding apparatus 300 may be used to create a syringe barrel 212 in a process comprising the following steps: injecting molten thermoplastic molding material into a syringe barrel-shaped molding space; retaining a predetermined portion of the impression member within the molding space so that the molding material forms around the portion of the impression member thereby creating a recess within a wall of the completed syringe barrel; and, after the molding material has been cooled to a sufficiently solid state, withdrawing the impression member from the recess, optionally in a direction perpendicular to the axial direction of movement of the actuator and/or perpendicular to the central axis of the inner core, to enable withdrawal of the completed syringe from the molding apparatus in an axial direction. Referring to FIG. 11A, it is contemplated that this process would result in a bypass groove 217 having sharp outer corners 219a.

Figure 11B:
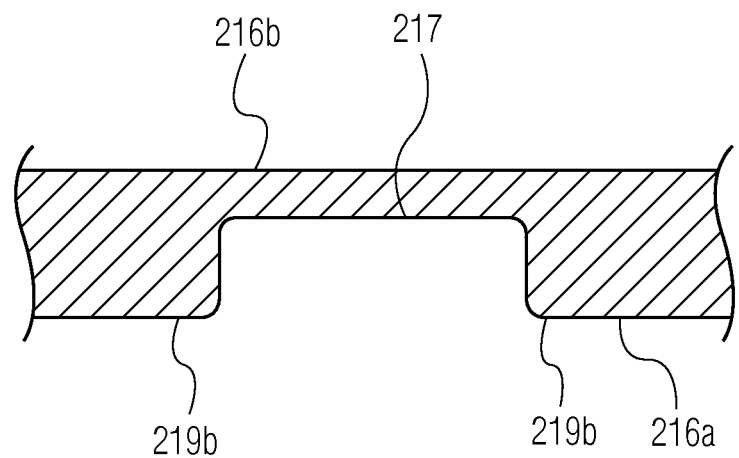
FIG. 11B is an enlarged cross sectional view of a bypass groove having rounded outer edges.

As an alternative, the molding apparatus 300 may be used to create a syringe barrel 212 in a process comprising the following steps: injecting molten thermoplastic molding material into a syringe barrel-shaped molding space; moving a predetermined portion of the impression member into the molding space to displace some of the molding material and thus create a recess within a wall of the completed syringe barrel; and, after the molding material has been cooled to a sufficiently solid state, withdrawing the impression member from the recess, optionally in a direction perpendicular the axial direction of movement of the actuator and/or perpendicular to the central axis of the inner core, to enable withdrawal of the completed syringe from the molding space in an axial direction. In one variation of this alternative, the molding space is substantially filled (e.g., 98%) with molding material and the impression member's creation of the recess displaces the molding material sufficiently to completely fill the molding space. In another variation of this alternative, the molding space is substantially filled (e.g., 96% to 99.5% by volume, optionally about 97%, optionally about 98%, optionally about 99%) with molding material, the impression member creates the recess, and additional molding material is injected to completely fill the molding space. Referring to FIG. 11B, it is contemplated that any variations of this alternative process would result in a bypass groove 217 having rounded outer corners 219b.

A skilled artisan would understand that other alternative process steps may also be used according to the spirit and scope of the present invention. Notably, whichever way the process is specifically carried out, the end result is preferably a thermoplastic (e.g., COC or COP) syringe barrel 212 without a line down its center because the barrel is formed from a solid one-piece mold and is withdrawn from the mold cavity in an axial direction.

Figure 12:
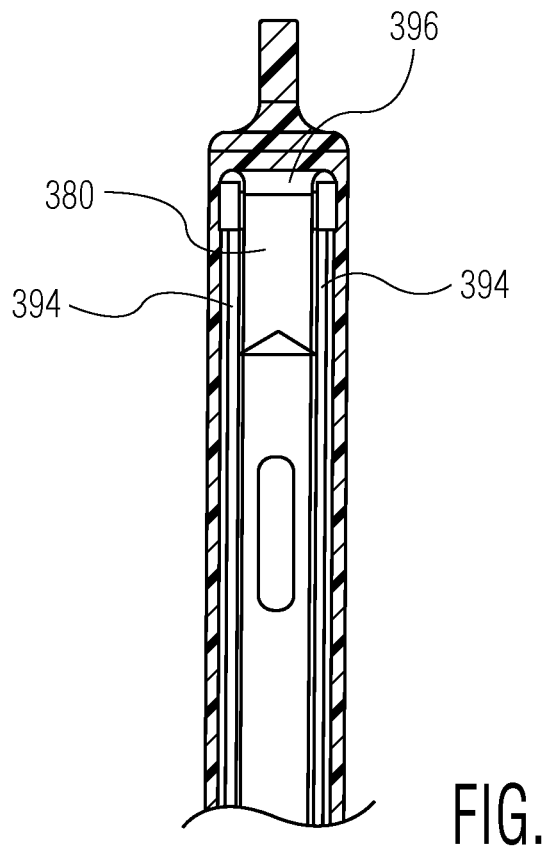
FIG. 12 is a cross sectional view of a portion of the inner core of the injection molding apparatus of FIGS. 8-10
Figure 13:
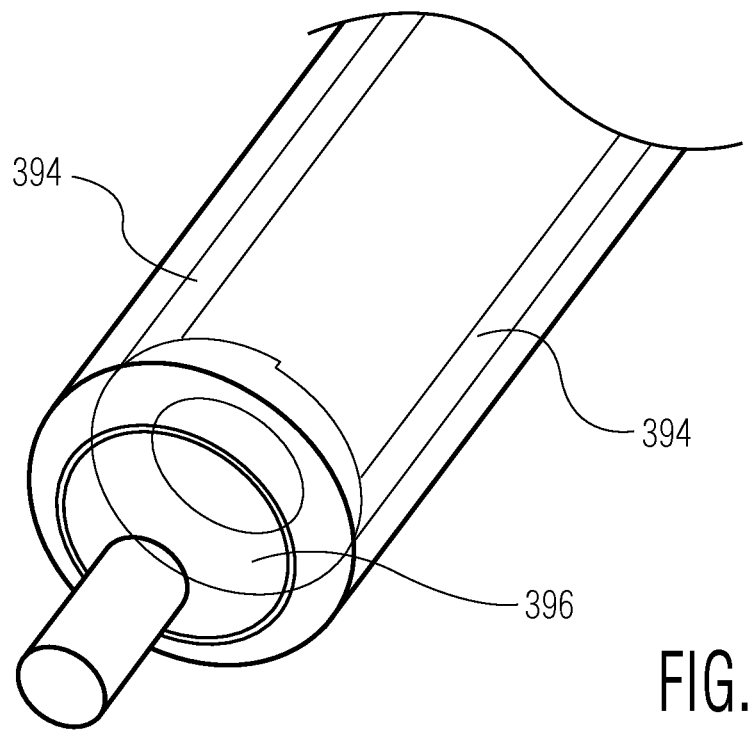
FIG. 13 is an enlarged internal perspective view of a portion of the inner core of FIGS. 8-10 and 12.

In order to regulate temperature of the molding material during the molding process, a plurality of cooling channels 394, shown in FIGS. 12 and 13, optionally run axially within the inner core 352. The cooling channels 394 are adjacent to the space 380 within the inner core 352 on one side and the molding space 354 on the other. The cooling channels 394 are optionally adapted to facilitate the flow of coolant, which absorbs heat from the molding material. The cooling channels 394 may empty into an optionally toroid or torus shaped hollow 396 at a far end of the inner core 352. This configuration permits continuous flow of the coolant through the inner core 352.

Barrier, pH Protective and Trilayer Coatings for Syringes

In another aspect, the invention includes use of syringes having a PECVD coating or PECVD coating set. This aspect of the invention will be discussed primarily in the context of a pre-filled syringe, particularly a dual-chambered syringe, as a preferred implementation of optional aspects of the invention. Again, however, it should be understood that the present invention may include any parenteral container having a bypass groove and that utilizes a plunger, partition and bypass in the inner wall, such as dual-chambered syringes, cartridges, auto-injectors, pre-filled syringes, pre-filled cartridges or vials.

For some applications, it may be desired to provide one or more coatings or layers to the interior wall of a parenteral container to modify the properties of that container. For example, one or more coatings or layers may be added to a parenteral container, e.g., to improve the barrier properties of the container and prevent interaction between the container wall (or an underlying coating) and drug product held within the container. It is contemplated that these coatings provide a parenteral package having the beneficial properties of both plastic and glass, without typical drawbacks possessed by each such material alone. This is a particularly unique concept and application in the field of dual chambered syringes.

Figure 7B:
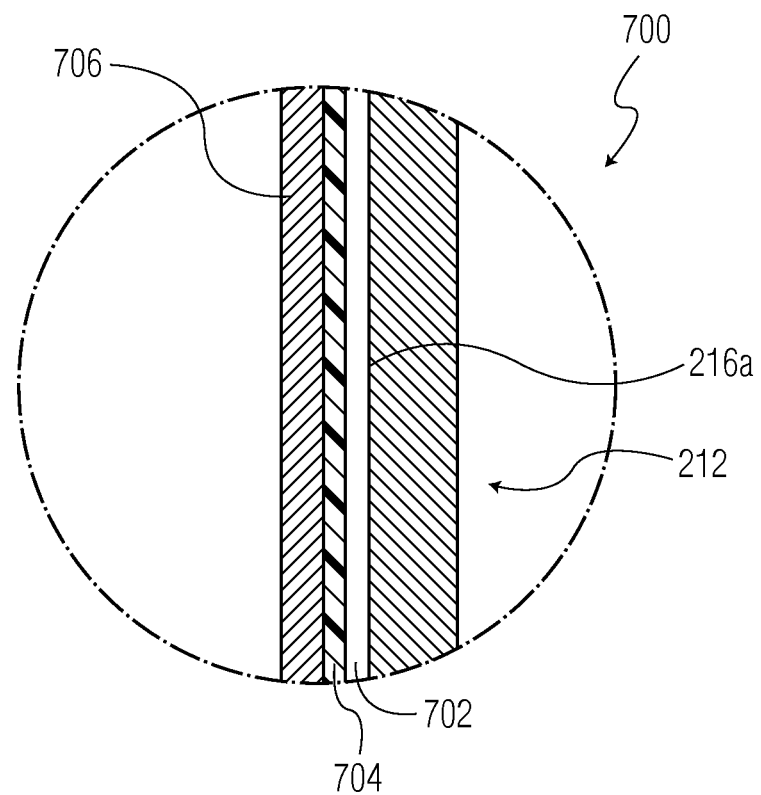
FIG. 7B is an enlarged view of the wall of the syringe barrel shown in FIG. 7 illustrating an optional trilayer coating set on the inner wall.

For example, as shown in FIG. 7B, which is a first alternative embodiment of an enlarged section view of the syringe barrel 212 of FIG. 7, the inner wall 216a of the syringe barrel 212 may include a coating set 700 comprising one or more coatings or layers. The barrel 212 may include at least one tie coating or layer 702, at least one barrier coating or layer 704, and at least one organo-siloxane coating or layer 706. The organo-siloxane coating or layer 706 preferably has pH protective properties. This embodiment of the coating set 700 is referred to herein as a "trilayer coating" in which the barrier coating or layer 704 of SiO$_x$ is protected against contents having a pH otherwise high enough to remove it by being sandwiched between the pH protective organo-siloxane coating or layer 706 and the tie coating or layer 702. The contemplated thicknesses of the respective layers in nm (preferred ranges in parentheses) are given in the following Trilayer Thickness Table:

| Trilayer Thickness Table | | |
| --- | --- | --- |
| Adhesion | Barrier | Protection |
| 5-100 | 20-200 | 50-500 |
| (5-20) | (20-30) | (100-200) |

Properties and compositions of each of the coatings that make up the trilayer coating are now described.

The tie coating or layer 702 has at least two functions. One function of the tie coating or layer 702 is to improve adhesion of a barrier coating or layer 704 to a substrate (e.g., the inner wall 216a of the barrel 212), in particular a thermoplastic substrate, although a tie layer can be used to improve adhesion to a glass substrate or to another coating or layer. For example, a tie coating or layer, also referred to as an adhesion layer or coating can be applied to the substrate and the barrier layer can be applied to the adhesion layer to improve adhesion of the barrier layer or coating to the substrate.

Another function of the tie coating or layer 702 is that when applied under a barrier coating or layer 704, the tie coating or layer 702 can improve the function of a pH protective organo-siloxane coating or layer 706 applied over the barrier coating or layer 704.

The tie coating or layer 702 can be composed of, comprise, or consist essentially of SiO$_x$C$_y$, in which x is between 0.5 and 2.4 and y is between 0.6 and 3. Alternatively, the atomic ratio can be expressed as the formula Si$_w$O$_x$C$_y$. The atomic ratios of Si, O and C in the tie coating or layer 289 are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33).

The atomic ratio can be determined by XPS. Taking into account the H atoms, which are not measured by XPS, the tie coating or layer 702 may thus in one aspect have the formula Si$_w$O$_x$C$_y$H$_z$ (or its equivalent S$_t$O$_x$C$_y$), for example where w is 1, x is from about 0.5 to about 2.4, y is from about 0.6 to about 3, and z is from about 2 to about 9. Typically, a tie coating or layer 702 would hence contain 36% to 41% carbon normalized to 100% carbon plus oxygen plus silicon.

The barrier coating or layer for any embodiment defined in this specification (unless otherwise specified in a particular instance) is a coating or layer, optionally applied by PECVD as indicated in U.S. Pat. No. 7,985,188. The barrier coating preferably is characterized as an "SiO$_x$" coating, and contains silicon, oxygen, and optionally other elements, in which x, the ratio of oxygen to silicon atoms, is from about 1.5 to about 2.9. The thickness of the SiO$_x$ or other barrier coating or layer can be measured, for example, by transmission electron microscopy (TEM), and its composition can be measured by X-ray photoelectron spectroscopy (XPS). The barrier layer is effective to prevent oxygen, carbon dioxide, or other gases from entering the container and/or to prevent leaching of the pharmaceutical material into or through the container wall.

Referring again to FIG. 7B, the barrier coating or layer 704 of SiO$_x$, in which x is between 1.5 and 2.9, may be applied by plasma enhanced chemical vapor deposition (PECVD) directly or indirectly to the thermoplastic inner wall 216a of the barrel 212 (in this example, a tie coating or layer 702 is interposed between them) so that in the filled syringe barrel 212, the barrier coating or layer 704 is located between the inner or interior surface of the inner wall 216a of the barrel 212 and the injectable medicine contained within the barrel 212.

Certain barrier coatings or layers 704 such as SiOx as defined here have been found to have the characteristic of being subject to being measurably diminished in barrier improvement factor in less than six months as a result of attack by certain relatively high pH contents of the coated vessel as described elsewhere in this specification, particularly where the barrier coating or layer directly contacts the contents. This issue can be addressed using an organo-siloxane coating or layer as discussed in this specification.

Preferred methods of applying the barrier layer and tie layer to the inner surface of the barrel 212 is by plasma enhanced chemical vapor deposition (PECVD), such as described in, e.g., U.S. Pat. App. Pub. No. 20130291632.

The Applicant has found that barrier layers or coatings of SiO$_x$ are eroded or dissolved by some fluids, for example aqueous compositions having a pH above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the SiO$_x$ coating. Optionally, this problem can be addressed by protecting the barrier coating or layer 704, or other pH sensitive material, with a pH protective organo-siloxane coating or layer 706.

Optionally, the pH protective organo-siloxane coating or layer 706 can be composed of, comprise, or consist essentially of Si$_w$O$_x$C$_y$H$_z$ (or its equivalent SiO$_x$C$_y$) or Si$_w$N$_x$C$_y$H$_z$ or its equivalent SiN$_x$C$_y$). The atomic ratio of Si:O:C or Si:N:C can be determined by XPS (X-ray photoelectron spectroscopy). Taking into account the H atoms, the pH protective coating or layer may thus in one aspect have the formula Si$_w$O$_x$C$_y$H$_z$, or its equivalent SiO$_x$C$_y$, for example where w is 1, x is from about 0.5 to about 2.4, y is from about 0.6 to about 3, and z is from about 2 to about 9.

Typically, expressed as the formula Si$_w$O$_x$C$_y$, the atomic ratios of Si, O and C are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4)

Si 100: O 92-107: C 116-133 (i.e. w=1, x=0.92 to 1.07, y=1.16 to 1.33), or

Si 100: O 80-130: C 90-150.

Alternatively, the organo-siloxane coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer 706, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer 706 can be increased in comparison to the organosilicon precursor, and/or the atomic ratio of oxygen to silicon can be decreased in comparison to the organosilicon precursor.

An exemplary empirical composition for a pH protective coating according to the present invention is $SiO_{1.3}C_{0.8}H_{3.6}$.

Optionally in any embodiment, the pH protective coating or layer 706 comprises, consists essentially of, or consists of PECVD applied silicon carbide.

Optionally in any embodiment, the pH protective coating or layer 706 is applied by employing a precursor comprising, consisting essentially of, or consisting of a silane. Optionally in any embodiment, the silane precursor comprises, consists essentially of, or consists of any one or more of an acyclic or cyclic silane, optionally comprising, consisting essentially of, or consisting of any one or more of silane, trimethylsilane, tetramethylsilane, Si2-Si4 silanes, triethyl silane, tetraethyl silane, tetrapropylsilane, tetrabutylsilane, or octamethylcyclotetrasilane, or tetramethylcyclotetrasilane.

Optionally in any embodiment, the pH protective coating or layer 706 comprises, consists essentially of, or consists of PECVD applied amorphous or diamond-like carbon. Optionally in any embodiment, the amorphous or diamond-like carbon is applied using a hydrocarbon precursor. Optionally in any embodiment, the hydrocarbon precursor comprises, consists essentially of, or consists of a linear, branched, or cyclic alkane, alkene, alkadiene, or alkyne that is saturated or unsaturated, for example acetylene, methane, ethane, ethylene, propane, propylene, n-butane, i-butane, butane, propyne, butyne, cyclopropane, cyclobutane, cyclohexane, cyclohexene, cyclopentadiene, or a combination of two or more of these. Optionally in any embodiment, the amorphous or diamond-like carbon coating has a hydrogen atomic percent of from 0.1% to 40%, alternatively from 0.5% to 10%, alternatively from 1% to 2%, alternatively from 1.1 to 1.8%.

Optionally in any embodiment, the pH protective coating or layer 706 comprises, consists essentially of, or consists of PECVD applied SiNb. Optionally in any embodiment, the PECVD applied SiNb is applied using a silane and a nitrogen-containing compound as precursors. Optionally in any embodiment, the silane is an acyclic or cyclic silane, optionally comprising, consisting essentially of, or consisting of silane, trimethylsilane, tetramethylsilane, Si2-Si4 silanes, triethylsilane, tetraethylsilane, tetrapropylsilane, tetrabutylsilane, octamethylcyclotetrasilane, or a combination of two or more of these. Optionally in any embodiment, the nitrogen-containing compound comprises, consists essentially of, or consists of any one or more of: nitrogen gas, nitrous oxide, ammonia or a silazane. Optionally in any embodiment, the silazane comprises, consists essentially of, or consists of a linear silazane, for example hexamethylene disilazane (HMDZ), a monocyclic silazane, a polycyclic silazane, a polysilsesquiazane, or a combination of two or more of these.

Optionally in any embodiment, the PECVD for the pH protective coating or layer 706 is carried out in the substantial absence or complete absence of an oxidizing gas. Optionally in any embodiment, the PECVD for the pH protective coating or layer 706 is carried out in the substantial absence or complete absence of a carrier gas.

Optionally an FTIR absorbance spectrum of the pH protective coating or layer 706 SiOxCyHz has a ratio greater than 0.75 between the maximum amplitude of the Si—O—Si symmetrical stretch peak normally located between about 1000 and 1040 cm−1, and the maximum amplitude of the Si—O—Si asymmetric stretch peak normally located between about 1060 and about 1100 cm−1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment.

Optionally, in any embodiment the pH protective coating or layer 706, in the absence of the medicament, has a non-oily appearance. This appearance has been observed in some instances to distinguish an effective pH protective coating or layer 706 from a lubricity layer (e.g., as described in U.S. Pat. No. 7,985,188), which in some instances has been observed to have an oily (i.e. shiny) appearance.

The pH protective coating or layer 706 optionally can be applied by plasma enhanced chemical vapor deposition (PECVD) of a precursor feed comprising an acyclic siloxane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. Some particular, non-limiting precursors contemplated for such use include octamethylcyclotetrasiloxane (OMCTS).

Optionally, an FTIR absorbance spectrum of the pH protective coating or layer 706 of composition SiOxCyHz has a ratio greater than 0.75 between the maximum amplitude of the Si—O—Si symmetrical stretch peak between about 1000 and 1040 cm−1, and the maximum amplitude of the Si—O—Si asymmetric stretch peak between about 1060 and about 1100 cm−1.

Other precursors and methods can be used to apply the pH protective coating or layer 706 or passivating treatment. For example, hexamethylene disilazane (HMDZ) can be used as the precursor. HMDZ has the advantage of containing no oxygen in its molecular structure. This passivation treatment is contemplated to be a surface treatment of the SiOx barrier layer with HMDZ. To slow down and/or eliminate the decomposition of the silicon dioxide coatings at silanol bonding sites, the coating must be passivated. It is contemplated that passivation of the surface with HMDZ (and optionally application of a few mono layers of the HMDZ-derived coating) will result in a toughening of the surface against dissolution, resulting in reduced decomposition. It is contemplated that HMDZ will react with the —OH sites that are present in the silicon dioxide coating, resulting in the evolution of NH3 and bonding of S—(CH3)3 to the silicon (it is contemplated that hydrogen atoms will be evolved and bond with nitrogen from the HMDZ to produce NH3).

Another way of applying the pH protective coating or layer 706 is to apply as the pH protective coating or layer 706 an amorphous carbon or fluorocarbon coating, or a combination of the two.

Amorphous carbon coatings can be formed by PECVD using a saturated hydrocarbon, (e.g. methane or propane) or an unsaturated hydrocarbon (e.g. ethylene, acetylene) as a precursor for plasma polymerization. Fluorocarbon coatings can be derived from fluorocarbons (for example, hexafluoroethylene or tetrafluoroethylene). Either type of coating, or a combination of both, can be deposited by vacuum PECVD or atmospheric pressure PECVD. It is contemplated that that an amorphous carbon and/or fluorocarbon coating will provide better passivation of an SiOx barrier layer than a siloxane coating since an amorphous carbon and/or fluorocarbon coating will not contain silanol bonds.

It is further contemplated that fluorosilicon precursors can be used to provide a pH protective coating or layer 706 over an SiOx barrier layer. This can be carried out by using as a precursor a fluorinated silane precursor such as hexafluorosilane and a PECVD process. The resulting coating would also be expected to be a non-wetting coating.

Yet another coating modality contemplated for protecting or passivating an SiOx barrier layer is coating the barrier layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resin on an SiOx barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting an SiOx layer is to apply as a pH protective coating or layer 706 a liquid-applied coating of a polyfluoroalkyl ether, followed by atmospheric plasma curing the pH protective coating or layer 706. For example, it is contemplated that the process practiced under the trademark TriboGlide® can be used to provide a pH protective coating or layer 706 that is also provides lubricity.

Thus, a pH protective coating for a thermoplastic syringe wall according to an aspect of the invention may comprise, consist essentially of, or consist of any one of the following: plasma enhanced chemical vapor deposition (PECVD) applied silicon carbide having the formula SiOxCyHz, in which x is from 0 to 0.5, alternatively from 0 to 0.49, alternatively from 0 to 0.25 as measured by X ray photoelectron spectroscopy (XPS), y is from about 0.5 to about 1.5, alternatively from about 0.8 to about 1.2, alternatively about 1, as measured by XPS, and z is from 0 to 2 as measured by Rutherford Backscattering Spectrometry (RBS), alternatively by Hydrogen Forward Scattering Spectrometry (HFS); or PECVD applied amorphous or diamond-like carbon, CHz, in which z is from 0 to 0.7, alternatively from 0.005 to 0.1, alternatively from 0.01 to 0.02; or PECVD applied SiNb, in which b is from about 0.5 to about 2.1, alternatively from about 0.9 to about 1.6, alternatively from about 1.2 to about 1.4, as measured by XPS.

Figure 7C:
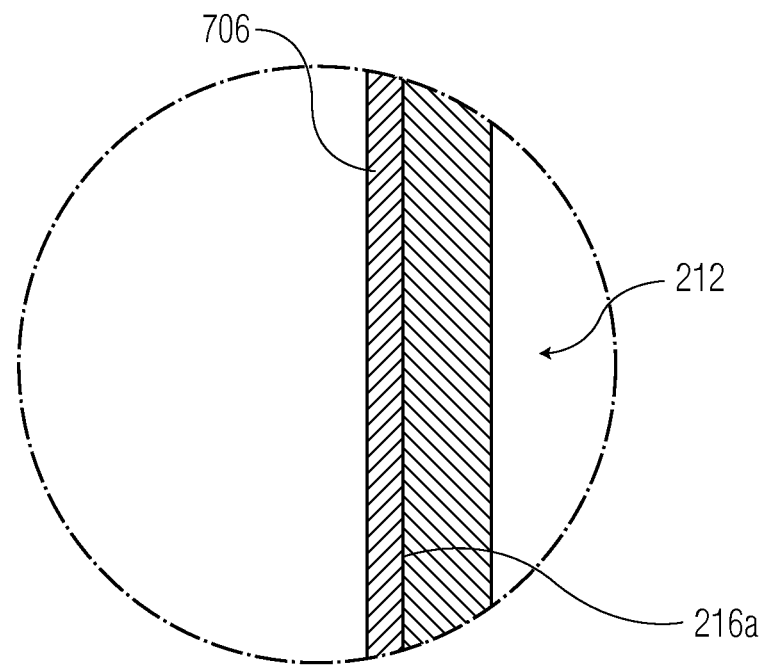
FIG. 7C is an enlarged view of the wall of the syringe barrel shown in FIG. 7 illustrating an optional pH protective coating on the inner wall.

Referring now to FIG. 7C, there is shown a second alternative embodiment of an enlarged section view of the syringe barrel 212 of FIG. 7. As shown in FIG. 7C, the syringe barrel 212 may include a organo-siloxane coating or layer 706 disposed directly on the inner wall 216a of the syringe barrel 212, rather than, e.g., as a top layer of a coating set. Optionally, the organo-siloxane coating or layer 706 has pH protective properties. Thus, optionally, the invention may involve use of a organo-siloxane coating or layer as a plunger-contacting and partition contacting surface, whether the organo-siloxane coating or layer is the top-most layer of a coating set or is by itself disposed directly onto the barrel wall.

PECVD apparatus suitable for applying any of the PECVD coatings or layers described in this specification, including the tie coating or layer 702, the barrier coating or layer 704 or the organo-siloxane coating or layer 706, is shown and described in U.S. Pat. No. 7,985,188 and U.S. Pat. App. Pub. No. 20130291632, both of which are incorporated herein by reference in their entireties. This apparatus optionally includes a vessel holder, an inner electrode, an outer electrode, and a power supply. A vessel seated on the vessel holder defines a plasma reaction chamber, optionally serving as its own vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

Processes for Injection Molding Alternative Walled Structures

Figure 14:
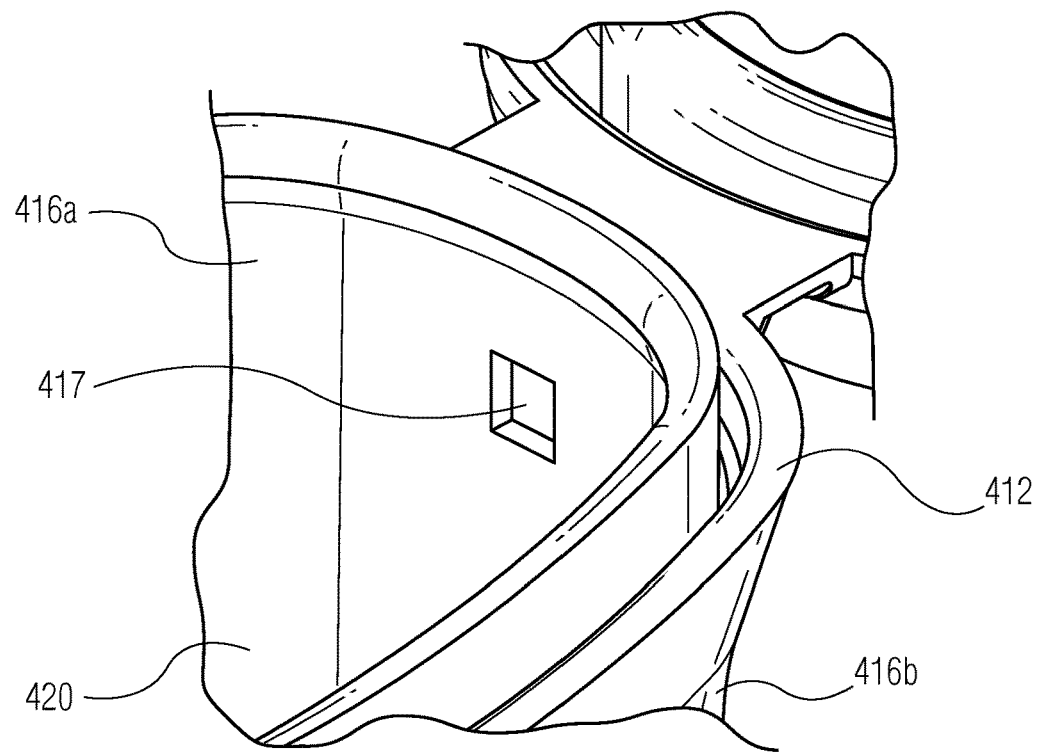
FIG. 14 is an enlarged perspective view of an opened vial according to the present invention.

The present invention is not limited to syringes, cartridges and other similar tubular thin-walled structures. Processes and molding assemblies according to the present invention may be broadly used to create an impression or recess in the internal wall of any injection molded product having an opening in at least one end, e.g., containers, vials, test-tubes, ampules, pipes, cups, etc. For example, there is shown in FIG. 14 a plastic vial 412, according to the present invention, having a small recess 417 in the internal wall 416a thereof. The recess 417 may be used, for example, to receive and retain a second part, e.g., a dispensing orifice for controlled flow of the vial's contents.

Figure 15:
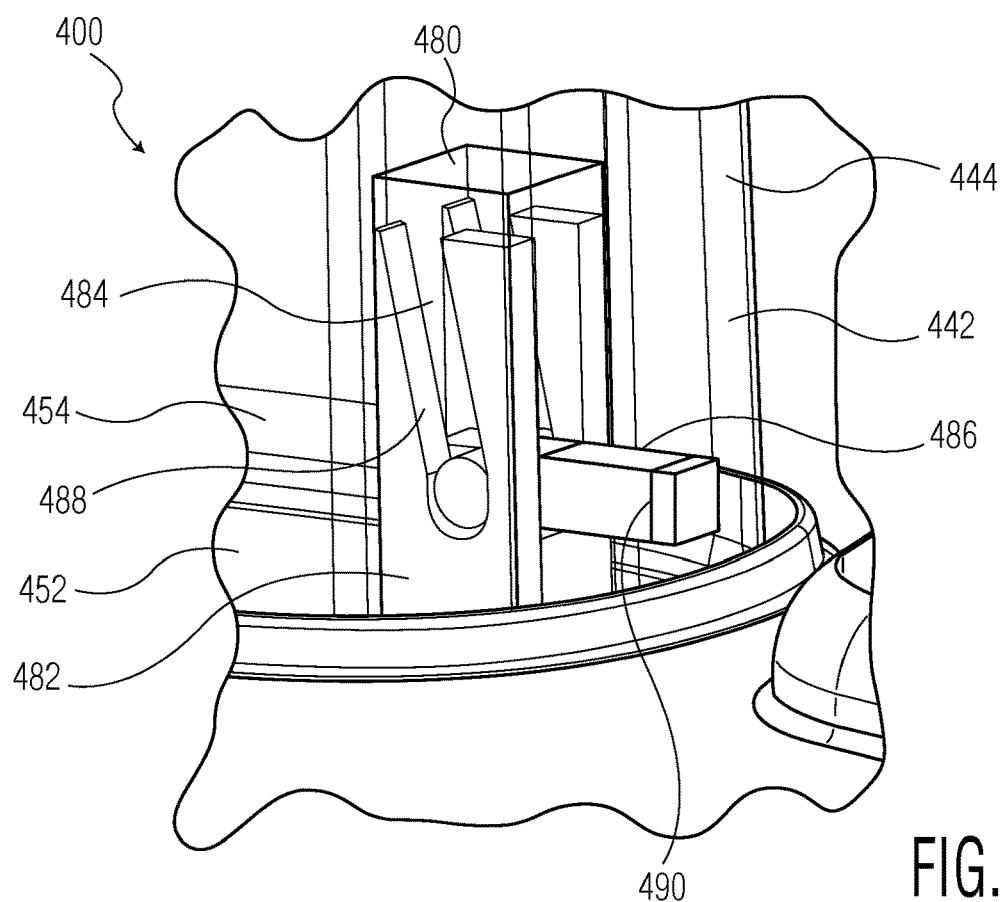
FIG. 15 is an enlarged perspective view of an injection molding apparatus for molding the vial of FIG. 14 with an actuator in an extended position.
Figure 16:
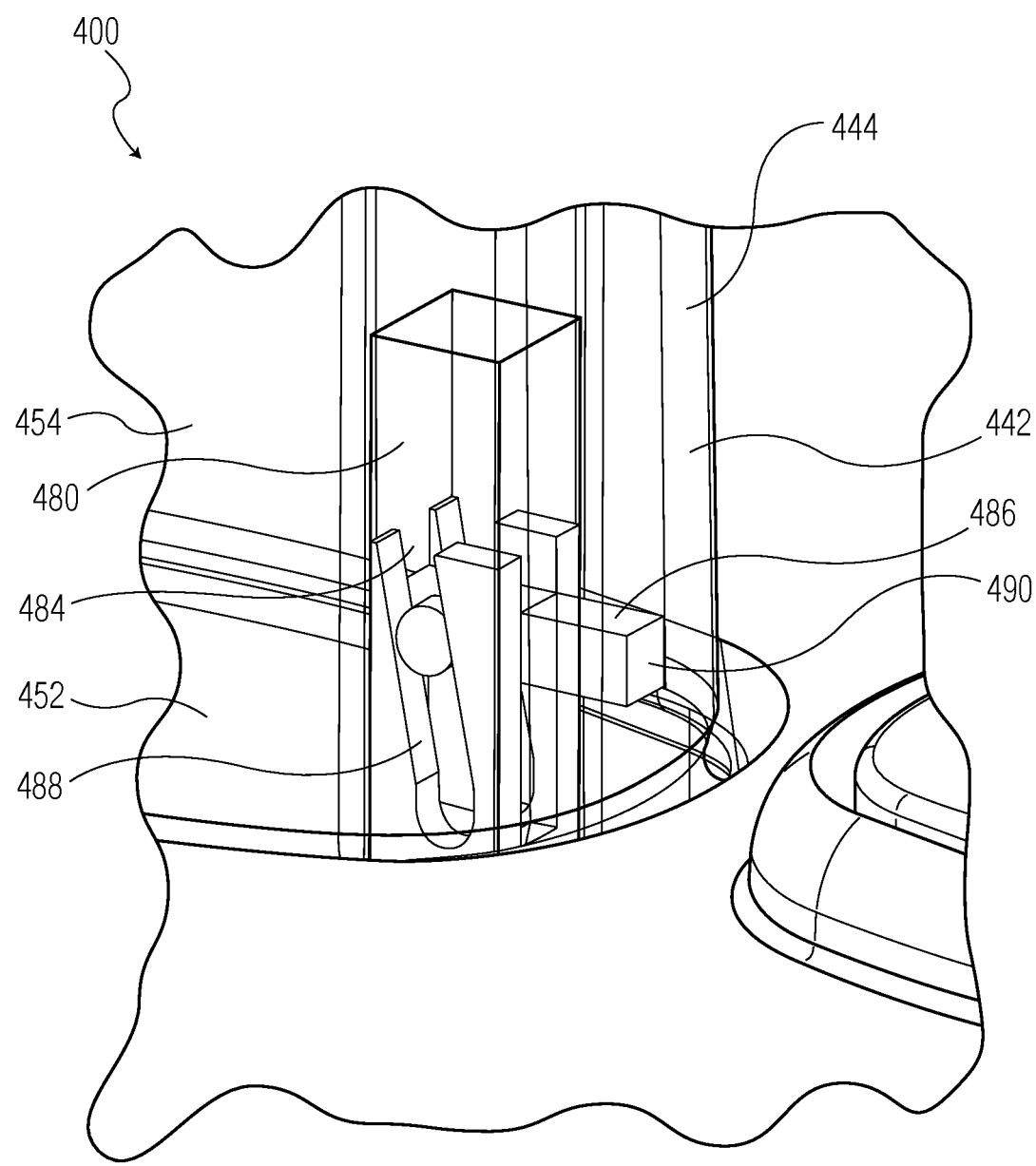
FIG. 16 is an enlarged perspective view of the injection molding apparatus of FIG. 15 with the actuator in a retracted position.

The vial 412 may be injection molded by implementing similar techniques and components used to fabricate the syringe barrel 212, as discussed above. Referring to FIGS. 15 and 16, there is shown the end portion of an injection molding apparatus 400 for molding the vial 412. The apparatus 400, which may be integrated into, e.g., a molding assembly similar to that used for making the syringe barrel 212, includes a mold cavity 442 adapted to receive molten thermoplastic material for forming the vial 412. The mold cavity 442 is preferably constructed of a solid one-piece mold block as opposed to being formed from joining together two separate mold blocks. This preferred feature would enable the vial 412 to be withdrawn axially once it is complete.

The mold cavity 442 is formed from a vial-shaped opening 444 of a molding block of the molding assembly. An inner core 452 fits within the opening 444 to define the interior 420 of the vial 412. The inner core 452 is vial-shaped, substantially like the opening 444, but has slightly smaller dimensions. A molding space 454 is defined between the opening 444 and the inner core 452. The molding space 454 is sized and shaped to form the vial 412. To fabricate the vial 412, melted thermoplastic material is injected into the molding space 454.

Within the inner core is a space 480 having a generally rectangular cuboid actuator 482 disposed therein, the actuator 482 being axially movable within the space 480. The actuator 482 may be slidable from an extended position within the space 480, as shown in FIG. 15, to a retracted position, as shown in FIG. 16. The actuator 482 may include a slot portion 484 having an impression member 486 slidably disposed therein. The slot portion 484 includes a ramp 488. In use, when the actuator 482 is in its extended position, as shown in FIG. 15, the impression member 486 is seated on a raised section of the ramp 488. In this position, the impression member 486 protrudes slightly through a window 490 in the inner core 452 and presses into the molten plastic in the molding space 454 to form an impression in the inner wall 416a of the vial 412. This impression constitutes the recess 417, e.g., as shown in FIG. 14, in the completed vial 412. This recess 417 is preferably located entirely within the inner wall 416a of the vial and does not bulge outward from the outer wall 416b. When the actuator 482 is in its retracted position, as shown in FIG. 16, the impression member 486 is seated on a lowered section of the ramp 488. In this position, the impression member 486 is withdrawn from the molten plastic, optionally in a direction perpendicular the axial direction of movement of the actuator and/or perpendicular to the central axis of the inner core, and the impression member's profile is contained entirely within the inner core 452. The impression member 486, as shown in FIG. 16, does not interfere with the material in the molding space 454. Thus, when the vial 412 is sufficiently cool and in solid form, the vial 412 may be withdrawn from the molding apparatus 400 in an axial direction. The process steps to make the vial 412 substantially resemble those carried out to make the syringe barrel 212.

While the invention has been described in detail and with reference to specific examples thereof, it will be apparent to one skilled in the art that various changes and modifications can be made therein without departing from the spirit and scope thereof.

What is claimed is:

1. A process for making a medical barrel using an injection molding apparatus, the apparatus having a molding space formed between a mold cavity and an inner core disposed within the mold cavity, the molding space defining a shape of the medical barrel, the process comprising the steps of:
   a. first injecting thermoplastic molding material into the molding space so as to substantially, but not completely, fill the molding space with the thermoplastic molding material;
   b. second, during or after injecting thermoplastic molding material into the molding space so as to substantially, but not completely, fill the molding space with the thermoplastic molding material, moving at least a portion of a movable impression member to protrude from the inner core into a portion of the molding space so as to create a bypass groove within an inner wall of the medical barrel; and
   c. third, retracting the impression member into the inner core in a direction perpendicular to the central axis of the inner core, such that the impression member is cleared from the molding space and housed entirely within the inner core, the process further comprising providing an actuator disposed within the inner core, wherein the actuator is operatively connected to the impression member and wherein movement of the actuator along the central axis of the inner core operates to retract the impression member.

2. The process of claim 1 further comprising a step of withdrawing the medical barrel from the molding space, after the medical barrel is solidified, in an axial direction.

3. The process of claim 2, wherein the mold cavity is formed from a solid one-piece mold block.

4. The process of claim 2, wherein the bypass groove, after the medical barrel is solidified, is located entirely within the inner wall and does not bulge outwardly from an outer wall of the medical barrel.

5. The process of claim 4, wherein the medical barrel, after it is solidified, does not have a line down its center as an artifact of the process.

6. The process of claim 2, the inner core comprising therein a longitudinal space, the actuator being disposed within the longitudinal space and being axially movable therein between an extended position of the actuator and a retracted position of the actuator.

7. The process of claim 6, the inner core comprising a window through which a portion of the impression member protrudes when the actuator is in the extended position of the actuator, wherein the impression member is movable to the retracted position of the impression member when the actuator is in the retracted position of the actuator.

8. The process of claim 6, the actuator including a slot portion, wherein a portion of the impression member is slidably disposed on:
   a. a track within the slot portion, the track running axially along a portion of the actuator at an incline; and/or
   b. a ramp on which the impression member is seated, wherein at least a portion of the ramp comprises an incline.

9. The process of claim 8, wherein the impression member is slidably disposed on both the track and the ramp, wherein the track and the ramp include inclined portions that are substantially parallel to each other.

10. The process of claim 2, wherein the bypass groove is perpendicular to a central axis of the medical barrel.

11. The process of claim 2, wherein the bypass groove has a substantially constant cross section.

12. The process of claim 2, wherein the bypass groove has rounded outer corners.

13. The process of claim 2, further comprising a step of applying, in a plasma enhanced chemical vapor deposition (PECVD) process, a trilayer coating set to the inner wall of the medical barrel.

14. The process of claim 2, wherein the step of injecting thermoplastic molding material into the molding space so as to substantially, but not completely, fill the molding space with the thermoplastic molding material, comprises filling 96% to 99.5% of the volume of the molding space with the thermoplastic molding material.

15. The process of claim 14, wherein the step of moving at least a portion of a movable impression member to protrude from the inner core into a portion of the molding space so as to create a bypass groove within an inner wall of the medical barrel, displaces the thermoplastic molding material sufficiently to completely fill the molding space with the thermoplastic molding material.

16. The process of claim 15, wherein the bypass groove has rounded outer corners.

17. The process of claim 16, wherein the bypass groove, after the medical barrel is solidified, is located entirely within the inner wall and does not bulge outwardly from an outer wall of the medical barrel.

18. The process of claim 14, further comprising, after the step of moving at least a portion of a movable impression member to protrude from the inner core into a portion of the molding space so as to create a bypass groove within an inner wall of the medical barrel, injecting additional thermoplastic molding material into the molding space to as to completely fill the molding space.

19. The process of claim 18, wherein the bypass groove has rounded outer corners.

20. The process of claim 19, wherein the bypass groove, after the medical barrel is solidified, is located entirely within the inner wall and does not bulge outwardly from an outer wall of the medical barrel.

* * * * *